Figure 1:
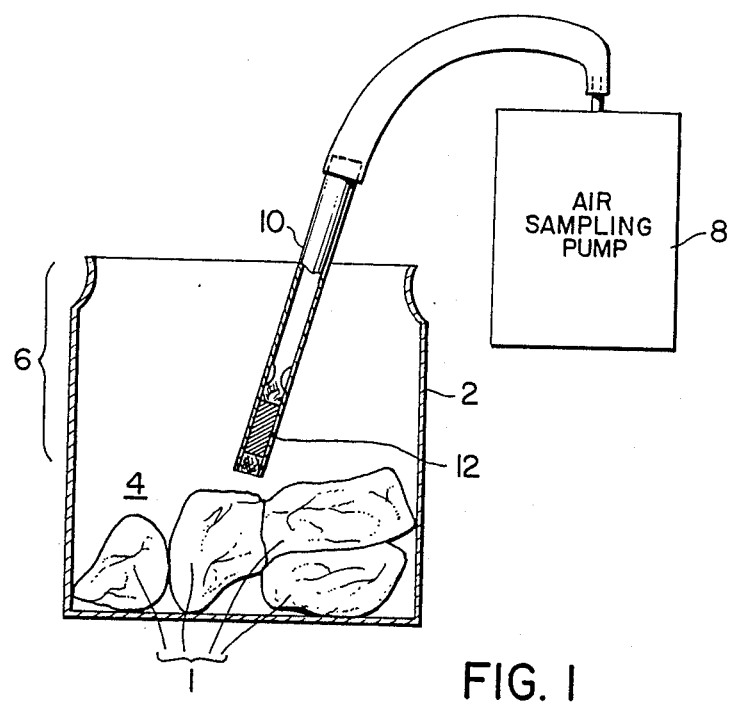

United States Patent [19]

Elias et al.

[11] Patent Number: 4,980,294

[45] Date of Patent: Dec. 25, 1990

[54] METHOD FOR TESTING THE FRESHNESS OF FISH

[75] Inventors: Lorne Elias, Nepean; Marek E. Krzymien, Gloucester, both of Canada

[73] Assignee: National Research Council of Canada/Conseil National de Recherches du Canada, Ottawa, Canada

[21] Appl. No.: 401,780

[22] Filed: Sep. 1, 1989

[51] Int. Cl.⁵ .............................................. G01N 33/12
[52] U.S. Cl. ........................................ 436/21; 426/231
[58] Field of Search .................... 73/23.1, 23, 27 R; 436/21; 435/21; 426/231; 324/71.1

[56] References Cited

U.S. PATENT DOCUMENTS

| | | | |
|---|---|---|---|
| 4,080,821 | 3/1978 | Johnston | 73/27 R |
| 4,309,185 | 1/1982 | Simon et al. | 436/21 |
| 4,650,752 | 3/1987 | Ohashi et al. | 435/21 X |
| 4,758,778 | 7/1988 | Kristinsson | 324/65 R |

FOREIGN PATENT DOCUMENTS 240160  10/1986  Japan ..................................... 436/21

Primary Examiner—Hezron E. Williams
Assistant Examiner—Joseph W. Roskos
Attorney, Agent, or Firm—Francis W. Lemon

[57] ABSTRACT

A simple but precise procedure for measuring fish freshness in terms of trimethylamine (TMA) headspace concentration of a fish sample is provided based on air sampling the headspace with Carbotrap ® or Tenax ® sorbent tubes and subsequent thermal desorption and gas chromatographic analysis. The sampling and analysis are completed in less than five minutes. Fish freshness as determined by the TMA headspace concentration is consistent with the grading estimated by organoleptic tests, but the instrumental method provides a more objective and quantitative assessment of quality and an estimation of the post mortem age of the fish.

5 Claims, 1 Drawing Sheet

METHOD FOR TESTING THE FRESHNESS OF FISH

This invention relates to a method of testing the freshness of fish.

Most species of marine fish and shellfish produce in their digestive process trimethylamine oxide (TMAO) which plays a role in osmoregulation. In frozen fish TMAO is reduced by endogenous enzymes to dimethylamine (DMA) and formaldehyde whereas in fresh or iced fish it is reduced by bacterial enzymes to trimethylamine (TMA), see, for example:

Regenstein, J. M., M. A. Schlosser, A. Samson and M. Fey. 1982. Chemical changes of trimethylamine oxide during fresh and frozen storage of fish, p. 137–148. In R. E. Martin, G. J. Flick, C. E. Hebard and D. R. Ward (ed.) Chemistry and Biochemistry of Marine Food Products. AWI Publishing Company, Westport, CT.;

Castell, C. M., B. Smith and W. Neal. 1971. Production of dimethylamine in muscle of several species of godoid fish during frozen storage, especially in relation to presence of dark muscle. J. Fish. Res. Board Can. 28:1–5;

Lundstrom, R. C. and L. D. Racicot. 1983. Gas chromatographic determination of dimethylamine and trimethylamine in seafoods. J. Assoc. Off Anal. Chem. 66:1158–1163; and Hebard, C. E., G. J. Flick and R. E. Martin. 1982. Occurrence and significance of trimethylamine oxide and its derivatives in fish and shellfish. p. 149–187. In R. E. Martin, G. J. Flick, C. E. Hebard and D. R. Ward (ed.) Chemistry and Biochemistry of Marine Food Products. AWI Publishing Company, Westport, CT.

The concentration of the amines in fish tissue is both time and temperature dependent, and is therefore related to the deterioration of the fish.

The concentration of the amines is presently determined through chemical analysis of the fish tissue. The Dyer's colorimetric method and its numerous modifications, see, for example:

Dyer, W. J. and Y. A. Monsey. 1945. Amines in fish muscle. II. Development of trimethylamine and other amines. J. Fish Res. Board Can. 6:359–367;

Dyer, W. J. 1950. Note on colorimetric estimation of trimethylamine. J. Fish. Res. Board Can. 7:576–579;

Dyer, W. J. 1959 Report on trimethylamine in fish. J. Assoc. Off. Anal. Chem. 42:292–294;

Murray, C. K. and S. M. Gibson. 1972. An investigation of the method of determining trimethylamine in fish muscle extracts by the formation of its pictrate salt. J. Fd. Technol. 7:35–46. Part I and 7:47–51 Part II;

Simmon, F. J. and W. B. Slater. 1982. Chemical analysis for quality determination of tuna. U.S. Pat. No. 4,309,185;

Bullard, F. A. and J. Collins. 1980. An improved method to analyze trimethylamine in fish and the interference of ammonia and dimethylamine. Fish. Bull. 78:465–73;

Hashimoto, Y. and T. Okaichi. 1957. On the determination of trimethylamine oxide. A modification of the Dyer method. Bull, Jap. Soc. Sci. Fish. 23:269–272; and Tozawa, H., K. Enokibara and K. Amano. 1970. Effect of dimethylamine on the value of trimethylamine determined by Dyer's method. Bull, Jap. Soc. Sci. Fish. 36:606–611, are best known and, although laborious, are widely used.

Murray, C. K. and J. R. Burt, 1964, Proceedings of the Technical International Symposium in London, Torry Research Station, Aberdeen, Memoir—no. 225, teaches a method for the automated determination of TMA based on the colour change of an indicator solution into which TMA vapour is injected.

Wong, K. and T. A. Gill, 1987, Enzymatic determination of trimethylamine and its relationship of fish quality, J. Fd. Sci. 52:103, teaches a procedure for the determination of TMA based on the oxidation of TMA with phenazine methasulfate in the presence of TMA dehydrogenase.

It has also been proposed to determine trimethylamine in fish tissue by gas chromatography, see:

Ritskes, T. M. 1975 The gas chromatographic determination of trimethylamine and dimethylamine in fish, fishery products and other foodstuffs. J. Fd. Technol. 10:221–228;

Dunn, S. R., M. L. Simenhoff and L. G. Wesson Jr. 1976. Gas chromatographic determination of free mono-, di, and trimethylamines in biological fluids. Anal. Chem. 48:41–44;

Hiatt, M. H. 1983. Determination of volatile organic compounds in fish samples by vacuum distillation and fused silica capillary gas chromatography/mass spectrometry. Anal. Chem 55:506–516.

Lundstrom, R. C. and L. D. Racicot. 1983. Gas chromatographic determination of dimethylamine and trimethylamine in seafoods. J. Assoc. Off. Anal. Chem. 66:1158–1163.

Stockemer, von J. and R. Kruse. 1985. Neue Methoden zur Bestimmung von TVB-N bzw. TMA-N in Fischen und Fischerzeugnissen. Archiv. Fuer Lebensmittelhygiene 36:116–17.

Gas chromatography has also been proposed for use in the determination of amines in air. The air sample is either injected directly into the gas chromatograph, see Fujii, T. and T. Kitai, 1987, Determination of trace levels of trimethylamine in air by gas chromatography/surface ionization organic mass spectrometry, Anal. Chem. 59:379–382; or preconcentrated on a solid sorbent, see Kuwata, K., E. Akiyama, Y. Yamazaki, M. Yamasaki and Y. Kuge, 1983, Trace determination of low molecular weight aliphatic amines in air by gas chromatography, Anal. Chem. 55:2199–2201, wherein the amines were trapped in a cartridge containing a special sorbent and eluted with a methanol-water mixture before gas chromatographic analysis. Amines trapped on solid sorbents have also been thermally desorbed into gas chromatographs, see Kashihira, N., K. Kirita, Y. Watawabe and K. Tamata, 1980, Gas chromatographic measurement of N-containing compounds; determination of trimethylamine in ambient air with Tenax-GC preconcentration and chemiluminescent nitrogen detector-gas chromatography, Bunseki Kagaku 29:858, where a Tenax-GC ® sorbent is used; and Fuselli, S., G. Benedetti and R. Mastrangeli, 1982, Determination of methylamines in air using charcoal traps and gas chromatographic analysis with alkali flame detector (AFD), Atmospheric Environment, 16:2943–2946, where activated charcoal traps are used.

The chemical methods for the determination of fish freshness, although precise and objective, are time consuming, require laboratory space and must be performed by technically qualified personnel.

According to the present invention there is provided a method of testing the freshness of fish, comprising:

(a) placing the fish at a predetermined temperature in a container having an interior which is substantially free of trimethylamine and which encompasses a trimethylamine collecting, gaseous head space above the fish, then (b) maintaining the fish in the container until a concentration in the gaseous headspace of enzymatically produced trimethylamine, emanating from the fish, equilibrates, then (c) withdrawing a known volume of the trimethylamine containing gaseous headspace, through an adsorption tube having a sample carrying end capable of adsorbing trace amounts of trimethylamine thereon, until substantially all of the trimethylamine from the known volume is adsorbed thereon, then (d) thermally desorbing the adsorbed sample from the sample carrying end into a stream of a carrier gas, then (e) determining the freshness of the fish from the quantity of trimethylamine in the carrier gas.

Preferably the quantity of trace trimethylamine in the carrier gas is determined by gas chromatography.

In some embodiments of the present invention the adsorption tube is a glass tube. The fish is preferably maintained in the container at a constant and known temperature until the concentration in the gaseous headspace of enzymatically produced trimethylamine, emanating from the fish, equilibrates.

The fish to be tested may comprise well mixed samples from the front, rear and mid-sections of a fish or a fish fillet.

Figure 2:
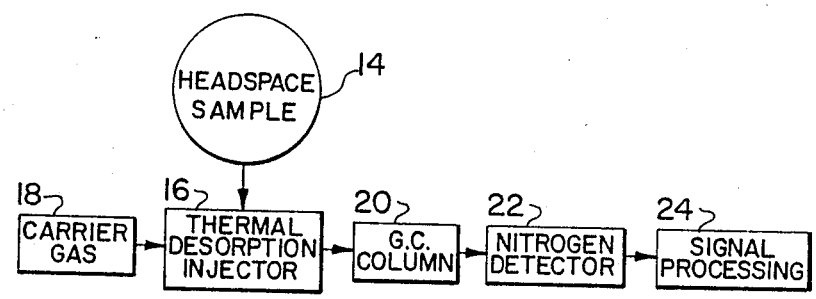

In the accompanying drawings which illustrate, by way of example, an embodiment of the present invention, FIG. 1 is a diagrammatic side view of a headspace sampling arrangement, and FIG. 2 is a block diagram of a method of determining the quantity of trimethylamine in a headspace sample on a solid sorbent from the arrangement shown in FIG. 1.

In FIGS. 1 and 2, a method of testing the freshness of fish in the form of fish chunks 1 (FIG. 1) is shown, comprising:

(a) placing the fish chunks 1 at a predetermined temperature in a container jar 2 having an interior 4 which is substantially free of trimethylamine and which encompasses a trimethylamine collecting, gaseous headspace 6 above the fish chunks 1, then (b) maintaining the fish chunks 1 in the container jar 2 until a concentration in the gaseous headspace 4 of enzymatically produced trimethylamine, emanating from the fish chunks 1, equilibrates, then (c) withdrawing, by means of an air sampling pump 8, a known volume of the trimethylamine containing gaseous headspace 6, through an adsorption tube 10 having a sample carrying end 12 capable of adsorbing trace amounts of trimethylamine thereon, until substantially all of the trimethylamine 14 (FIG. 2) from the known volume is adsorbed thereon, then (d) thermally desorbing, by means of a thermal desorption injector 16, the adsorbed sample 14 from the sample carrying end 12 into a stream of a carrier gas from a source 18, then (e) determining, by means of a gas chromatograph 20, a thermionic ionization detector 22 and a signal processor 24, the freshness of the fish from the quantity of trimethylamine in the carrier gas.

In laboratory tests to verify the present invention, using the apparatus shown in FIGS. 1 and 2 the gas chromatograph 20 was a Varian 4600 ® gas chromatograph (GC) with Vista 401 ® Data Station. Field tests were carried out on a varian 1400 ® gas chromatograph (GC). Other details of the apparatus used were as follows:

Column of GC: 2 m × 2 mm I.D. glass or 1 m × 1.6 mm I.D. polytetrafluorethylene tube packed with 60/80 mesh Carbopack ® B/4% Carbowax ® 20M/0.8% KOH; carrier gas for the 4600 GC was He at 20 mL/min and for the 1400 GC was $N_2$ at 20 mL/min; column temperature isothermal at 75° C.

Detector 22: thermionic ionization at 190° C.; hydrogen flow 4.5 mL/min, air flow 175 mL/min; bead current 3.5 A, bias voltage −4V.

Adsorption tube 10: 76 mm × 6.4 mm O.D. Pyrex ® tube, packed with 35/60 mesh Tenax ® TA or 20/40 mesh Carbotrap ®; length of Tenax column 40 mm (4600 GC) or 10 mm (1400 GC); Carbotrap column 10 mm.

GC Injector: thermal desorption port at 180° C.

The injection ports of both GCs were modified to accept the glass adsorber tubes 10 for thermal desorption. The injection port of varian 4600 GC could also accommodate conventional microsyringe injections of liquid standards through the septum while the glass adsorber tube 10 was in place.

The injector port of the 1400 GC, which was used in the field trials, was identical in configuration to that described and claimed in U.S. patent application No. 07/268,489 filed Nov. 8, 1988, but was modified for use with glass adsorption tubes.

With both instruments a desorption temperature of 180° C. yielded sharp, symmetrical peaks of the amines and reproducible retention times.

Adsorption tubes 10 were used in headspace sampling of TMA and were also the means of injecting calibration solutions when a few microlitres were deposited onto the packing (Varian 1400 GC). Headspace samples were collected with a personal air sampling pump 8 (AeroVironment Inc.) with settable pumping speeds.

Calibration

Standard aqueous solutions of DMA-HCl, TMA-HCl and the internal standard n-propylamine (n-PA) hydrochloride were prepared by dissolving dried crystals in 1% HCl in a 100 mL volumetric flask. The concentration of free amine in the solutions was 1 mg/mL.

For internal standard calibration the standard solutions were analyzed in the same manner as fish tissue, except for the tissue extract being replaced by an equal volume of 4% (W/V) perchloric acid. Sixteen combinations of DMA-TMA concentrations in a range of 28.4–170.4 ng for DMA and 24.9–149.3 ng for TMA were analyzed to calibrate the instrument.

For headspace analysis an external standard calibration was used. A few microlitres of the toluene extracts (c.f. Fish Tissue Analysis) containing known amounts of TMA were analyzed to calculate the response factor.

Breakthrough Volume

The breakthrough volume of the adsorbers was determined by sampling TMA vapour of constant concentration from a dynamic vapour generator. A small air stream flowed over a 0.01% water solution of TMA, then mixed with a larger diluting air stream. The vapour in this stream was sampled for 0.5 to 3.0 minutes in 0.5 minute increments with an adsorber tube containing a 10 mm length of Tenax at a rate of 25, 50, 100 and 200 mL/min and with an adsorber having a 40 mm plug of the packing at a rate of 200 mL/min. With a 10 mm plug of Carbotrap in the adsorber the TMA vapour stream was sampled at 25, 50, 100, 200, 300, 400, 500 and 600 mL/min. The sample volume ranged from 12.5 mL to 1800 mL. To determine the trapping efficiency of the adsorber the vapour stream was sampled at rates of 200, 300 and 400 mL/min for sample volumes of 200 to 2000 mL with two Carbotrap adsorbers connected in series.

Fish Samples

In the laboratory tests the fish samples were cut from 'fresh' halibut bought in a local store. The time the fish was caught was unknown However, for the purposes of this test, the day of purchase was taken to be day 0 on the age (after capture) scale.

In the field tests, on the other hand, the samples were delivered for analysis by National Sea Products Limited, Nova Scotia, Canada, and their grade and, in some cases, post mortem age were known.

Headspace Analysis 50 g samples of fresh halibut fillet were placed in 12 screw-cap jars 2 (250 mL capacity) and stored in a refrigerator at 3° C. Every two or three days a jar 2 was removed from the refrigerator, warmed to room temperature (21°±1° C.), and a headspace sample taken; depending on the expected TMA concentration, 100-200 mL of the headspace was drawn through the Tenax TA adsorption tube 10. The adsorber was then inserted into the injection port of the GC 20 where TMA was thermally desorbed into the column and analyzed.

In the field tests the fish sample as received was also cut into several 50 g pieces, placed in a jar 2 then covered. After allowing 5-10 minutes for the vapours in the headspace 6 to equilibrate, a headspace sample was collected at an air sampling rate of 100 mL/min for one minute.

Fish Tissues Analysis

The same sample of fish which had been analyzed for headspace TMA concentration was blended with 100 mL 6% $HClO_4$ for two minutes. The homogenate was filtered through Whatman ® No. 1 paper into a 250 mL, volumetric flask. Solids were rinsed three times with 4% $HClO_4$. Two 2 mL aliquots of the filtrate were placed in 15 mL centrifuge tubes with screw caps. 200 uL of internal standard, 2 mL toluene and 2 mL 65% (W/V) KOH were added in this order. Tubes were capped and heated at 60° for 10 minutes, cooled and shaken for two minutes. After the layers separated 1 uL aliquot of the toluene layer was injected into the GC. The procedure is basically that of Lundstrom and Racicot (1983) which has been previously referred to. The most important of the few modifications introduced is the substitution of toluene for the benzene suggested in the original procedure.

Results and Discussion

GC Analysis

The column selected and the operating parameters of the gas chromatographs provided excellent resolution and peak shape of DMA and TMA. The column packing, though susceptible to degradation by atmospheric carbon dioxide, has proven to be quite durable, continuing to produce good quantitative results after three months of intensive air sample analysis. When the TMA peaks showed signs of tailing several injections of 1% $NH_4OH$ at 220° C. restored the column to optimal performance. As experienced in the field tests the column could also be reconditioned by several injections of TMA standard or even by one or two air samples of high TMA concentration, viz., substandard fish headspace.

Although glass is an excellent column material for laboratory instruments, it may not be rugged enough for portable, field instruments. Metals (stainless steel, nickel) on the other hand are too active for amine analysis. They strongly adsorb amines and small, badly shaped peaks are obtained. Polytetrafluoroethylene is both chemically inert and rugged. We have found that 1 m×2.6 mm I.D. polytetrafluoroethylene tube packed with Carbopack B/4% Carbowax 20M/0.8% KOH is well suited for amine analysis in a field instrument, although the packing deteriorates somewhat faster in a polytetrafluoroethylene tube than in the glass column, probably due to permeability of air (and $CO_2$) through the column walls. It is interesting that the performance of this column is greatly improved by silylation which is not used for Carbowax columns. On the silylated column sub-nanogram quantities of TMA produce sharp, nearly symmetrical peaks on a flat baseline in less than a minute.

Breakthrough Volume

Of the two sorbents that were investigated for use in TMA headspace sampling, i.e. Tenax TA and Carbotrap, the latter was not available at the outset of the study and for this reason most of the air sampling work reported below was done using Tenax TA.

The Tenax TA adsorbent used, while adequate, does not trap trimethylamine with high efficiency. The breakthrough volume, as determined for the 40 mm-long adsorber pacing, is about 200 mL at a sampling rate of 200 mL/min. The 10 mm-long adsorber packing used with the Varian 1400 GC had a breakthrough volume of less than 25 mL at a sampling rate of 25 mL/min, and even lower at higher sampling rates. In the present invention, however, this is not a serious drawback; if the sampling rate and the sampling time are specified for a fish-testing protocol, the differences in peak size for different samples can only be attributed to differences in headspace concentration.

The results of the tests conducted to determine the breakthrough volume of the 10 mm-long Tenax TA adsorber allowed the choice of the most practical sampling time and sampling rate. The amount of TMA collected at a sampling rate of 200 mL/min was lower than that collected at 100 mL for any given sampling time. On the other hand, while the breakthrough volumes at sampling rates of 50 mL/min and 25 mL/min were higher than that of 100 mL/min, the amount of TMA collected at the latter rate was the largest. 100 mL/min was therefore the preferred sampling rate since it offered the highest sensitivity for a given sampling time with the 10 mm Tenax TA adsorber.

Carbotrap was found to be a more efficient sorbent for trapping TMA from air. The 10 mm Carbotrap adsorber had a breakthrough volume of about 800-900 mL at sampling rates of up to 600 mL/min (FIG. 6). At the sampling rates of 200, 300 and 400 mL/min the adsorber trapped TMA from samples of up to 1000 mL/min with an efficiency of 90% or more.

Both Carbotrap and Tenax TA were found to have a low affinity to water and to low-boiling volatiles; thus, the chromatograms of the headspace analyses were quite 'clean', exhibiting only one peak (TMA) and a flat baseline.

Comparison of TMA Headspace Concentration with TMA Tissue Concentration

It was important in the development of a present fish testing protocol to determine the relation between the concentration of TMA in fish tissue and in the headspace above the tissue; even more important, of course, was the relation between the headspace concentration of TMA and the age of the fish after capture, i.e. the freshness of the fish.

In general, the TMA concentration in the headspace was seen to follow a similar pattern to that in the tissue, especially as far as the initial rapid rise is concerned.

It was also noted that the TMA concentration in tissue, after the onset of the steep rise, reached a maximum at the 8-day mark and thereafter decreased, whereas the headspace concentration, after a similar steep rise, continued to increase, although at a slower rate. A possible explanation of this dissimilarity may lie in a warming trend of the laboratory during the latter stages of the tests, which could have increased the headspace vapour content. The temperature fluctuation could have also caused the high headspace concentration at the 6-day point and the lower concentration at the 10-day point.

The temperature of the fish during headspace sampling has a pronounced effect on the TMA concentration. To eliminate this effect sampling should preferably be carried out at a constant temperature. Ice temperature, while readily achieved, was not used in the present study since it lowered the sensitivity of detection. The tests showed that the concentration at room temperature with the exception of fresh fish (6 days or less) was about 4-10 times that at ice temperature. To improve the sensitivity at ice temperature a larger headspace sample could be collected with a more efficient adsorber (e.g. Carbotrap).

Field Tests

The field tests were conducted at the National Sea Products Limited plant in Lunenburg, Nova Scotia, Canada, during the last week of June 1988.

Background TMA Level

The large-scale operation of the plant offered a good opportunity to measure the background level of TMA in several locations in and outside the building for comparative purposes.

The landed fish undergo preliminary quality control in a grading room before entering the plant. A relatively high TMA concentration found in this room, however, precluded the possibility of setting up a fish 'sniffer' there.

The cleanest air was found outside the building, on the dock beside a trawler unloading the fish.

The laboratory air was moderately contaminated with TMA. The level of TMA background here varied by about 25% over a period of two days (Table 1).

TABLE 1

TMA Background Levels in Plant Laboratory Air

| Date and Time | Peak Area (arbitrary units) |
|---|---|
| June 28, 15:04 | 44 |
| June 28, 16:25 | 27 |
| June 29, 11:52 | 46 |
| June 29, 12:14 | 55 |
| June 29, 15:41 | 60 |
| June 29, 16:48 | 42 |
| Average | 46 |
| Standard deviation | 12 |
| Coefficient of variation | 26% |

Precision of TMA Headspace Analysis

A sample of Grade 2 cod and a sample of Grade 2 pollock were repeatedly analyzed for TMA headspace concentration. The quantitative results expressed as peak areas in arbitrary units presented in Table 2 show good precision with a variance coefficient of 7.2% for cod and 4.4% for pollock.

TABLE 2

Precision of TMA Headspace Analysis in Field Test

| Test No. | Peak Area (arbitrary units) | |
|---|---|---|
|  | Grade 2 Cod | Grade 2 Pollock |
| 1 | 157 | 144 |
| 2 | 180 | 137 |
| 3 | 162 | 132 |
| Average | 166 | 138 |
| Standard deviation | 12 | 6 |
| Coefficient of variation | 7.2% | 4.4% |

The Grades as referred to were estimated organoleptically by qualified personnel of National Sea Products Limited.

Variation of TMA Level

The trimethylamine oxide content of live fish and subsequent TMA level in the tissue after capture may vary not only with the species but also with the season, size, age of the fish and the local environment. However, no indication of seasonal variations for herring, yellowtails, haddock or cod was found in the previously referred Hebard et al. 1982 publication.

In the present field tests no significant differences were observed in the headspace concentration of TMA for Grade 1 cod, salmon, flounder, yellowtail, catfish, Korean sole or pollock (Table 3). The concentration was at the level of the ambient background concentration (Table 1). By comparison, Grade 1 ocean perch, lemon sole, scallops and particularly grey sole gave TMA readings above the background level.

TABLE 3

TMA Level in a Headspace Above Fish Sample

| Fish Species | Peak Area (arbitrary units) | |
|---|---|---|
|  | Grade 1 | Grade 2 |
| Cat fish | 41 | 83 |
| Cod | 55;34;48 | 175;286;180;506 |
| Flounder | 32 | n/a |
| Grey sole | 283 | 545 |
| Korean sole | 42 | n/a |
| Lemon sole | 108 | n/a |
| Ocean perch | 68;179 | 545;752 |
| Pollock | 43;33 | 144;137 |
| Yellowtail | 34 | 108 |
| Scallops | 118;410 | n/a |

TABLE 3-continued

| TMA Level in a Headspace Above Fish Sample | | |
|---|---|---|
| | Peak Area (arbitrary units) | |
| Fish Species | Grade 1 | Grade 2 |
| Salmon | 18;14;19* | 130;718 |

*Analyzed in a laboratory with low TMA background level.

For Grade 2 fish the TMA level also varied with the species. Grade 2 catfish and yellowtail flounder gave TMA readings comparable to those of Grade 1 ocean perch, lemon sole or scallops but much lower than that of Grade 1 grey sole. Grade 2 cod and pollock headspace TMA level was usually lower than that of Grade 1 grey sole. Grade 2 ocean perch and grey sole produced high levels of TMA headspace concentrations.

The TMA headspace concentration exhibited some variation between samples of a species of the same grade (Table 3). The variation may be a result of a difference in post mortem age of the fish or, possibly, to non-representative sampling since the content of TMAO and consequently TMA is different for the dark and light tissue of the fish. To obtain a more representative sample, portions of the fillet from the front, rear and mid-sections should preferably be cut into strips (or chopped in a blender) and mixed well.

There is a clear and pronounced difference of TMA headspace concentration between grades of the same species of fish as the examples shown in Table 3 illustrate. The differences are far greater than variations from sample to sample within the same grade or than the usual scatter of analytical results. Sampling-and-analysis according to the present invention would therefore appear to allow the determination of TMA headspace concentration with sufficient precision to readily distinguish between grades of a given fish species.

The tests indicated that it is possible to measure quickly and precisely the TMA concentration in the headspace above fish tissue by the instrumental method described above, involving sorbent tube sampling and GC analysis; and that the time required for analysis need not exceed five minutes, including sampling.

The tests also indicated that there is a direct relationship between the TMA concentration in fish tissue and in the headspace. Fish freshness as determined by the TMA according to the present invention was found to be consistent with the grading estimated by organoleptic tests, but the instrumental method according to the present invention was found to provide a more objective and quantitative assessment of quality and an estimation of the post mortem age of the fish.

The TMA headspace concentration was found to be species-dependent. For example, the TMA headspace concentration of Grade 2 catfish and yellowtail flounder was found to be similar to that of Grade 1 lemon sole.

We claim:

1. A method of testing the freshness of fish, comprising:
   (a) placing the fish at a predetermined temperature in a container having an interior which is substantially free of trimethylamine and which encompasses a trimethylamine collecting, gaseous headspace above the fish, then
   (b) maintaining the fish in the container until a concentration in the gaseous headspace of enzymatically produced trimethylamine, emanating from the fish, equilibrates, then
   (c) withdrawing a known volume of the trimethylamine containing gaseous headspace, through an adsorption tube having a sample carrying end capable of adsorbing trace amounts of trimethylamine thereon, until substantially all of the trimethylamine from the known volume is adsorbed thereon, then
   (d) thermally desorbing the adsorbed sample from the sample carrying end into a stream of a carrier gas, then
   (e) determining the freshness of the fish from the quantity of trimethylamine in the carrier gas.

2. A method according to claim 1, wherein the quantity of trace trimethylamine in the carrier gas is determined by gas chromatography.

3. A method according to claim 1, wherein the adsorption tube is a glass tube.

4. A method according to claim 1, wherein the fish is maintained in the container at a constant and known temperature until the concentration in the gaseous headspace of enzymatically produced trimethylamine, emanating from the fish, equilibrates.

5. A method according to claim 1, wherein the fish to be tested comprises well mixed samples from the front, rear and mid-sections of a fish or a fish fillet.

* * * * *